United States Patent [19]

Meisert et al.

[11] 4,072,712
[45] Feb. 7, 1978

[54] PROCESS FOR THE PRODUCTION OF CARBODIIMIDES AND CARBODIIMIDE-ISOCYANATE ADDUCTS

[75] Inventors: Ernst Meisert, Leverkusen-Schlebusch; Peter Fischer, Cologne-Flittard, both of Germany

[73] Assignee: Bayer Aktiengesellschaft, Leverkusen, Germany

[21] Appl. No.: 751,839

[22] Filed: Dec. 17, 1976

Related U.S. Application Data

[63] Continuation of Ser. No. 381,102, July 20, 1973, abandoned, which is a continuation of Ser. No. 56,976, July 21, 1970, abandoned, which is a continuation-in-part of Ser. No. 623,818, March 17, 1967, abandoned.

[30] Foreign Application Priority Data

Mar. 18, 1966 Germany .............................. F48694

[51] Int. Cl.$^2$ .......................................... C07C 119/055
[52] U.S. Cl. .................................................. 260/566 R
[58] Field of Search ..... 260/566 R, 551 CD, 248 NS, 260/453 A

[56] References Cited
FOREIGN PATENT DOCUMENTS 1,514,803  1/1968  France ................................ 260/566

Primary Examiner—Gerald A. Schwartz
Attorney, Agent, or Firm—Gene Harsh; Joseph C. Gil

[57] ABSTRACT

Carbodiimides are prepared by reacting organic isocyanates at a temperature of at least 150° C. in the presence of a catalyst having the formula

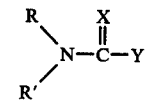

wherein
R and R' are the same or different and represent hydrogen, alkyl, aryl and when joined together form a heterocyclic ring;
Y is hydrogen, alkyl, chloroalkyl, aryl, alkoxyphosphono and

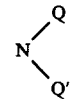

wherein Q is hydrogen, alkyl or aryl; Q' is hydrogen, alkyl, aryl, COR", and SO$_2$R" wherein R" is alkyl or aryl, and when Y is joined together with R, they form a heterocyclic ring; and X is oxygen or sulfur.

8 Claims, No Drawings

PROCESS FOR THE PRODUCTION OF CARBODIIMIDES AND CARBODIIMIDE-ISOCYANATE ADDUCTS

This application is a continuing application of Application Ser. No. 381,102, filed July 20, 1973 now abandoned, which in turn was a continuation of Application Ser. No. 56,976, filed July 21, 1970, now abandoned which in turn was a continuation-in-part of Application Ser. No. 623,818, filed Mar. 17, 1967, now abandoned, and relates to a process of preparing carbodiimide from organic isocyanates, and more particularly, to catalysts for the reaction which contains amide groups.

It is known that organic isocyanates can be converted into the corresponding carbodiimides by the action of organically substituted phosphine-, arsine- or stibine oxides in a reaction which is accompanied by the elimination of carbon dioxide. It is also known that carbodiimides can be obtained by heating organic isocyanates at elevated temperatures over long periods. Suitable catalysts for such reactions are organic phosphoric acid esters, phosphonates, phosphoric acid amides and phosphonic acid amides.

There are often objections to the use of compounds of arsenic, phosphorus and antimony on account of their physiological properties. In addition, the reaction products are often unstable if even minute traces of the catalysts are left behind in the products. Consequently, reaction products of this kind can only be used to a limited extent in practice.

On the other hand, processes based solely on thermal reactions require prolonged heating, yield dark-colored decomposition products and provide unsatisfactory yields. Metal compounds such as aluminum propoxide or heavy metal naphthenates, shorten the reaction time, but at the same time promote the formation of cyanurates which are undesired as secondary products.

It is therefore an object of this invention to provide an improved method of preparing carbodiimide. It is another object of this invention to provide new catalysts for the preparation of carbodiimides by reaction of isocyanates. It is another object of this invention to provide an improved process for preparing carbodiimides which avoids decomposition products.

The foregoing objects and others which will become apparent from the following description are accomplished in accordance with the invention generally speaking by providing a process of preparing carbodiimides or carbodiimide-isocyanate adducts by heating organic isocyanates at temperatures above about 150° C. in the presence of a catalytic amount of a compound having the formula

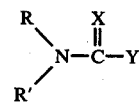

wherein
R and R' are the same or different and represent hydrogen, alkyl, aryl and when joined together form a heterocyclic ring;
Y is hydrogen, alkyl, chloroalkyl, aryl, alkoxyphosphono and

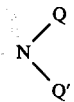

wherein Q is hydrogen, alkyl or aryl; Q' is hydrogen, alkyl, aryl, COR", and SO₂R" wherein R" is alkyl or aryl, and when Y is joined together with R, they form a heterocyclic ring; and X is oxygen or sulfur.

It is possible by using such catalysts to shorten the heating time very considerably and to avoid decomposition of the reaction products. The catalysts used for the process in question are physiologically acceptable compounds which only become active at temperatures above 150° C., so that the storage stability of the reaction products is not affected by the catalyst.

Some suitable aliphatic radicals are alkyl radicals such as for example, methyl, ethyl, n-propyl, isopropyl, n-butyl, isobutyl, sec-butyl, t-butyl, n-pentyl, methyl butyl, dimethyl propyl, ethyl propyl and the various positional isomers thereof including the corresponding straight and branched chain isomers of hexyl, heptyl, octyl, nonyl, decyl, undecyl, dodecyl, tridecyl, tetradecyl, pentadecyl, hexadecyl, heptadecyl, octadecyl, nondecyl, eicosyl and the like; substituted alkyl radicals, such as, for example chloromethyl, chloroethyl, chlorohexyl, chloromethoxy, chloroethoxy, methoxy phosphono, ethoxy phosphono, chloroethoxyphosphono and the like.

Some suitable aryl radicals are, for example, phenyl, a-napthyl, b-napthyl, a-anthryl, b-anthryl, g-anthryl, o-tolyl, m-tolyl, p-tolyl, indene isoindene, phenanthrene, napthacene, chrysene, pyrene, triphenylene and the like.

Any suitable catalyst within the above formula may be used for the process according to the invention, such as, for example urea, monomethylurea, N,N-dimethyl urea, N,N'-diethylurea, N,N'-diethyl-N-methylthiourea, diphenylurea, diphenylthiourea, N-methyl-N'-dimethylurea, N-phenyl-N'-ethylurea, phenylthiourea, N,N-diphenyl-N'-dimethylurea, tetramethylurea, 1,3,5-triphenylbiuret, 1,3-diphenyl-5,5'-dimethylbiuret, 1,3-diphenyl-allophanic acid methyl ester, formanilide, acetamide, methylacetamide, dimethyl acetamide, propionic acid morpholide, bis-(benzoyl)-piperazine, benzoyl piperazine, benzoyl piperidine, benzanilide, acetanilide, N-ethylbenzanilide, chloroacetamide, thioacetamide, thiobutyric acid anilide, maleic acid hydrazide, caprolactam, N-methylcaprolactam, dodecan lactam, phthalimide, isatin, 1,2,3, 6-tetrahydrophthalimide, naphtholactam-1,8 pyrrolidone-(2), piperazine-2,5-dione, saccharin, barbituric acid, diethylbarbituric acid, rhodamine, vinyl acetamide, p-toluene-sulphonylurea, N-phenylsulphonyl-N'-methylurea, N-phenyl-sulphonyl-N'-phenylurea, phenyl sulphonyl-N,N'-diphenylurea, 4-acetyl-aminobenzene-sulphonylurea, acetylpropionylurea or acetylbenzoylurea, N-acetyl-N-methylurea, benzoylthiourea, N-propionyl-N'-phenylurea, dimethoxy-phosphonoform methylanilide, diethoxyphosphonoform anilide, diethoxyphosphonoform naphthylamide, and bis-(2-chloroethoxy)-phosphonoform-N-methylanilide and the like.

It is evident from the foregoing that the catalyst composition suitable for use according to the invention comprise a broad range of compounds. However, it must be stressed that the activity of these compounds depends solely on the presence of the

group in the molecule, the substituent groups R, R' and Y being of little significance. Although numerous examples of preferred compounds are given above, it is to be understood that any compound having the given general formula is contemplated within the scope of the invention. It is of course evident that it would be impractical to specifically recite all of the possible compounds due to the variable nature of the substituent groups. It is again emphasized that the presence of the

group in the molecule is critical to the compounds functioning as a catalyst in the process of the invention.

The catalysts may themselves be added directly to the isocyanates in a catalytic amount and preferably in quantities of from about 0.05 to about 10 mol percent, and most preferably from about 0.2 to about 5 mol percent based on the isocyanates used. Alternatively the catalyst may be prepared in situ from the isocyanates or carbodiimides, for example, by adding the corresponding quantity of water, hydrogen sulphide, ammonia, aniline, 2,6-diisopropylaniline, morpholine, piperazine, ethanolamine, diethanolamine, acetic acid, butyric acid, thiobutyric acid, lactic acid, oxalic acid, salicylic acid, benzene-sulphonic acid amide, p-toluene sulphonic acid methylamide or benzene sulphonic acid.

Any suitable mono- or polyfunctional, aliphatic or aromatic isocyanate capable of carbodiimide formation is contemplated for use according to the invention. Illustrative of preferred isocyanates are monofunctional isocyanates, such as, for example, methylisocyanate, ethylisocyanate, propyl isocyanate, isopropylisocyanate, allylisocyanate, butylisocyanate, isobutylisocyanate, sec-butylisocyanate, tert-butylisocyanate, amylisocyanate, 3-methosypropylisocyanate, tetradecylisocyanate, chlorodecylisocyanate, 4-oxahexadecylisocyanate, 4-oxa-6-butyldodecylisocyanate, dodecylisocyanate, hexadecylisocyanate, octadecylisocyanate, 1-isocyanato-octadecene-9, xylyl isocyanate, phenylisocyanate, cyclohexylisocyanate, o-chlorophenylisocyanate, m-chlorophenylisocyanate, p-chlorophenylisocyanate, o-toluylisocyanate, m-toluylisocyanate, p-toluylisocyanate, o-ethylphenylisocyanate, o-ethoxyphenylisocyanate, p-ethoxyphenylisocyanate, o-nitrophenylisocyanate, m-nitrophenylisocyanate, p-nitrophenylisocyanate, benzylisocyanate, 2,4-dichlorophenylisocyanate, 3,4-dichlorophenylisocyanate, 2,5-dichlorophenylisocyanate, a-naphthylisocyanate, b-naphthylisocyanate, o-biphenylisocyanate, o-phenoxyphenylisocyanate, 3-nitro-4-chlorophenylisocyanate and the like.

Polyfunctional isocyanates, such as, for example ethylene diisocyanate, propylene diisocyanate, butylene diisocyanate, pentylene diisocyanate, methylbutylene diisocyanate, hexamethylene diisocyanate, tetra-methylene diisocyanate, penta-methylene diisocyanate, dipropyldiisocyanato ether, heptamethylene diisocyanate, 2,2-dimethylpentylene diisocyanate, 3-methoxyhexamethylene diisocyanate, octamethylene diisocyanate, 2,2,4-trimethylpentylene diisocyanate, 3-butoxyhexamethylene diisocyanate, 1,3-dimethyl benzene diisocyanate, 1,4-dimethylbenzene diisocyanate, 1,2-dimethylcyclohexane diisocyanate, 1,4-dimethylcyclohexane diisocyanate, 1,4-diethylbenzene diisocyanate, 1,4-dimethylnapthalene diisocyanate, 1,5-dimethylnapthalene diisocyanate, 1-methylisocyanate 2-n-propylisocyanate 3,5-dimethylcyclohexane, cyclohexane-1,3-diisocyanate, cyclohexane-1,4-diisocyanate, 1-methylcyclohexane-2,4-diisocyanate, 1-methylcyclohexane-2,2-diisocyanate, 1-ethylcyclohexane-2,4-diisocyanate, dicyclohexylmethane-4,4'-diisocyanate, dicyclohexylmethylmethane-4,4'-diisocyanate, dicyclohexyl-dimethylmethane-4,4'-diisocyanate, 2,2-dimethyldicyclohexylmethane-4,4'-diisocyanate, 3,3'-5,5'-tetramethyldicyclohexylmethane-4,4'-diisocyanate, 4-phenylisocyanatemethylisocyanate, 1-chlorobenzyl-2,4-diisocyanate, 1,3-dichlorobenzyl-4,6-diiosocyanate, 1,4-dichlorobenzyl-2,5-diisocyanate, 1-chloro-4-methoxybenzyl-2,5-diisocyanate, 1-methoxybenzyl-2,4-diisocyanate, 1-methyl-4-methoxybenzyl-2,5-diisocyanate, 1-ethoxybenzyl-2,4-diisocyanate, 1,3-dimethoxybenzyl-4,6-diisocyanate, 1,4-dimethoxybenzyl-2,5-diisocyanate, 1-propoxybenzyl-2,4-diisocyanate, 1-isobutoxybenzyl-2,4-diisocyanate, 1,4-diethoxybenzyl-2,5-diisocyanate, toluene-2,4-diisocyanate, toluene-2,6-diisocyanate, diphenylether-2,4-diisocyanate, naphthalene-1,4-diisocyanate, 1,1'-dinaphthalene-2,2'-diisocyanate, biphenyl-2,4-diisocyanate, 3,3'-dimethylbiphenyl-4,4'-diisocyanate, 3,3'-dimethoxybiphenyl-4,4'-diisocyanate, diphenylmethane-4,4'-diisocyanate, diphenylmethane-2,4'-diisocyanate, diphenylmethane-2,2'-diisocyanate, 3-nitrotriphenylmethane-4,4'-diisocyanate, pyrene-3,8-diisocyanate, chrysene-2,8-diisocyanate, naphthalene-1,3,7-triisocyanate, diphenylmethane-2,4,4-triisocyanate, 3-methyldiphenylmethane-4,6,4'-triisocyanate, 4,4'-dimethyldiphenylmethane-2,2',5,5'-tetraisocyanate, triphenylmethane-4,4'-4''-triisocyanate, and the like.

Aliphatic isocyanates, which are distinguished in the absence of catalysts by their outstanding stability and their sluggishness in reaction, naturally react more slowly than aromatic isocyanates. In general, the reaction time is shortened to from one quarter to one hundredth of the reaction time without catalyst, depending upon the quantity in which the catalyst is used.

The process according to the invention is advantageously carried out as follows: the organic isocyanate to be reacted is mixed with 0.1 to 2 mol percent of catalyst, after which the temperature is raised. At temperature above 150° C. evolution of carbon dioxide begins and increases as the temperature rises. The course of the reaction can be followed by measuring the quantity of gas evolved or by titrating the NCO-concentration, while the reaction itself can be controlled by temperature regulation. As soon as the required conversion has been obtained, the reaction mixture is cooled to a temperature below 150° C., as a result of which the reaction immediately stops. The reaction can be reinitiated, and hence controlled, by renewed heating at elevated temperature.

The reaction may also be carried out in the presence of inert solvents, for example, o-dichloro-benzene, a-chloronaphthalene or decahydronaphthalene. In some instances, it is of advantage to add porous substances, such as silica gel, active carbon or porous clay, in order to obtain uniform evolution of the carbon dioxide.

In cases where it is desired to isolate the carbodiimide, the reaction product is worked up in the usual way, for example, by vacuum distillation. In many instances, the end products are surprisingly pure in themselves, i.e., without special purification. The reaction of polyisocyanates is accompanied by the formation of hard synthetic resins after it has progressed beyond a certain extent.

If the carbodiimides formed are cooled, and providing free NCO-groups are still present in the reaction mixture, carbodiimide-isocyanate adducts are formed in the cold. These adducts can be reversibly split up into the carbodiimides and isocyanates at elevated temperatures.

If, therefore, the reaction of the polyisocyanates is suspended by cooling after 5 to 33 percent of the NCO-group have reacted, valuable isocyanate-carbodiimide adducts containing free isocyanate group are formed. By reaction with hydroxyl-group-containing polyesters or polyethers, polyfunctional alcohols or amines, they yield high-grade plastics, foam plastics, coating materials or pourable sealing compounds. The products obtained by the process and their reaction products with amines, are valuable auxiliaries for controlling the fabrication of compact homogeneous, cellular or porous plastics of the polyurethane or polyurea type.

The invention will be further illustrated by the following examples in which parts are by weight unless otherwise specified.

EXAMPLE 1

Batches, each comprising about 1000 parts (4 mols) of 4,4′-diphenylmethane diisocyanate are mixed at about 80° C. with the specified quantity of catalysts from Table 1 and the resulting mixture is heated for about 1 hour at about 225° C. The reaction times required for the reaction of about 25 percent of the original NCO-content to form carbodiimides, are determined by titrating the NCO-content.

Table 1

| Batch | Catalyst | Quantity (mol %) | Time in Minutes | Color of the Product |
|---|---|---|---|---|
| a | acetamide | 5 | 30 | yellow |
| b | N,N′-diphenylthiourea | 2.5 | 90 | lt.brown |
| c | urea | 2.5 | 120 | pale yellow |
| d | acetanilide | 5 | 45 | lt.brown |
| e | N-methylacetanilide | 5 | 35 | yellow |
| f | caprolactam | 5 | 60 | lt.brown |
| g (control) | none | 0 | 1200 | black-brown |

EXAMPLE 2

Batches each comprising about 1000 parts (4 mols) of an industrial mixture of 90 percent of 4,4′-diphenylmethane diisocyanate and 10 percent of 2,4′-diphenylmethane diisocyanate, are each mixed at about 50° C. with about 0.2 mols of water, acetic acid, butylamine or tetramethylurea, and the resulting mixture is heated at about 190° C. In contrast to the control test (no catalyst added) in which the required NCO-value of 25 percent was reached after about 48 hours, the test in which 0.1 mol of water is added showed a drop in the NCO-content to 23 percent after only three hours. The addition of about 0.2 mol of acetic acid cut the reaction time from about 48 hours to about 90 minutes. About 0.2 mol of di-n-butyl-amine shortened it to about 180 minutes, while 0.1 mol of tetramethylurea shortened the reaction time to only a few minutes.

EXAMPLE 3

Examples 1 and 2 are repeated. The amount of $CO_2$ evolved is measured and used as the criterion for the reaction velocity. The results of measurement show an outstanding consistency between the amount of the $CO_2$ measured and the NCO-decrease. This proves that the catalysts only accelerate carbodiimides formation and do not promote trimerization into cyanurates.

The infrared spectrum of the reaction products shows the band characteristic of carbodiimides and their NCO-addition compounds at 4.8 and 5.8μ. After the reaction products had been stored for a brief period, the absorption bands at 4.8μ disappears almost completely, while the infrared spectrum shows an intensified band at 5.8μ because the products were stabilized by the formation of isocyanate-carbodiimide adducts.

If the products were mixed with an excess of primary or secondary amine, for example, dibutylamine, and the excess amine is subsequently distilled off in vacuo the band at 5.8μ also disappears in addition to the absorption band at 4.3μ characteristic of NCO. New bands are observed at 6.1, 6.7 and 7.65μ. The fact that the trimers of isocyanates (cyanurates) which absorb at 5.8 to 5.95μ are not split under the reaction conditions, prove that such compounds are not formed as secondary products.

To test the stability of the products obtained by the process, they were stored for a period of several weeks at a temperature of about 30° C. There is no change either in viscosity or in the NCO-content during this period. A control test in which a product prepared from 4,4′-diphenylmethane diisocyanate under the action of 1-phenyl-3-methyl-1-phosphacyclopentane(3)-P-oxide, is stored, has to be terminated after two days because a high gas pressure had been built up in the tightly sealed vessel and because the product had solidified into a hard, insoluble mass.

EXAMPLE 4

About 1000 part batches of 4,4′-diphenylmethane diisocyanate are heated at 220° – 225° C.,
a. without any additives (control)
b. with 32 parts of phenyldimethylurea
c. with 11.6 parts of tetramethylurea
d. with 34.2 parts of benzene-sulphonic acid methylamide
e. with 46.6 parts of benzene-sulphonic acid anilide The amount of carbon dioxide evolved and the drop in the NCO-concentration are both measured.

| Batch | Reaction time (minutes) | Parts by Volume $CO_2$ (at NTP) | NCO-content |
|---|---|---|---|
| a | 60 | 500 | — |
|   | 210 | 2,010 | — |
|   | 420 | 4,800 | — |
| b | 210 | 9,620 | 21.2% |
| c | 60 | 10,950 | 20.3% |
| d | 420 | 9,380 | 22.8% |
| e | 90 | 13,200 | 27.0% |
| a | 1380 | 13,300 | 27.08 |

The reaction products show the characteristics absorption bands, all liquid at room temperature and do not solidify after storage for six weeks at 0° C., while the starting product crystallizes rapidly at 37.5° C.

EXAMPLE 5

About 2 mols (336 parts) of hexamethylene diisocyanate are heated at about 230° C. with about 0.02 mol (4.86 parts) of dimethoxyphosphonoform-N-methylanilide. The NCO-content drops from 49.5 percent to 30.0 percent in four hours, accompanied by the evolution of carbon dioxide. The temperature is then lowered to 149° – 150° C. and kept at this level for about two hours. There is no further drop in the NCO-content. The infrared spectrum shows the bands characteristic of carbodiimides and isocyanate-carbodiimide adducts.

Preparation of the dimethoxyphosphonoform-N-methylanilide used as catalyst in this Example About 1.5 mols of trimethyl phosphite are mixed at about 80° C. with about 1 mol of N-methylphenylcarbamic acid chloride, and the resulting mixture is heated for about 2½ hours at about 110° C. About 1 mol of methyl chloride is collected in a cooled receiver. Excess trimethyl phosphate is then distilled off in vacuo. Dimethoxyphosphonoform-N-methylanilide is left as residue in the form of a yellowish oil.

Analysis: C = 49.53%; H = 5.98%; P = 12.75%.
(Calculated: C = 49.5%; H = 5.81%; P = 12.75%).

EXAMPLE 6

About 1000 parts of an industrial mixture of about 65 parts of 2,4-toluene diisocyanate and about 35 parts 2,6-toluene diisocyanate, are heated at 220° – 225° C. with about 32.8 parts of phenyldimethylurea. The NCO-content falls from 46.5 percent to 37.6 percent in about 4½ hours. The infrared spectrum showed the bands characteristic of isocyanatecarbodiimide adducts. In a control test with no catalyst, the NCO-content falls to 46.1 percent over the same period.

EXAMPLE 7

About 4 mols (640 parts) of 1,4-benzene diisocyanate are mixed at about 96° C. with about 0.2 mols (3.6 parts) of water and then heated at about 225° C. There is a rapid drop in the NCO-content, accompanied by vigorous evolution of $CO_2$. About 1.2 mols of carbon dioxide is evolved after only 1 hour.

EXAMPLE 8

About 2 mol batches of phenyl isocyanates are heated at about 160° C. with about 0.02 mol of
a. diethoxyphosphonoform-diphenylamide
b. dimethoxyphosphonoform-N-methyl-N-a-naphthyl-formamide
c. diethoxyphosphono-ethyl formamide
d. diethoxyphosphono-dimethyl formamide After 50 percent of the theoretical quantity of carbon dioxide is evolved, the reaction product is distilled in vacuo. In addition to 1 mol of phenyl isocyanate diphenyl carbodiimide (b.p. 134° – 136° at 2 Torr) is obtained in excellent yields.

| Batch | Reaction time required | Yield % of theoretical |
|---|---|---|
| a | 6 hours | 96.8 |
| b | 6 hours | 98.2 |
| c | 11 hours | 95.1 |
| d | 7 hours | 96.7 |
| control | 26 hours | 75.3 |

EXAMPLE 9

About 1000 parts of 4,4'-diisocyanato diphenyl methane are mixed at about 70° C. with about 5 mol % of a catalyst. The mixture is subsequently heated to about 220° C. The reaction is stopped after about 25% of the NCO groups initially present in the reaction mixture are converted into carbodiimide groups. The reaction is controlled by titration.

| catalyst | time (min.) for 25% conversion | color |
|---|---|---|
| 9a None | 1220 | black-brown |
| 9b barbituric acid | 48 | yellow |
| 9c 1-phenyl-imidazolone-2 | 140 | light-yellow |
| 9d phthalimide | 230 | dark-brown |
| 9e saccharin | 248 | brown |

EXAMPLE 10

About 500 parts of a mixture of about 90% by weight of 4,4'-diisocyanato diphenyl methane and about 10% by weight of 2,4'-diisocyanato diphenyl methane are mixed at about 50° C. with 0.2 mol of a catalyst. The mixture is subsequently heated to about 190° C. The reaction was stopped after conversion of about 25% of the NCO groups initially present into carbodiimide groups. The reaction was controlled by titration of the NCO content.

| catalyst | time (min.) for 25% conversion | color |
|---|---|---|
| 10 a None | 1860 | dark-brown |
| 10 b stearylamide | 120 | light-yellow |
| 10 c p-dodecyl-aniline | 110 | light-yellow |
| 10 d 6-chlor-hexylamine-1 | 280 | yellow |
| 10 e 3-chlor-n-propionic acid amide | 275 | yellow |
| 10 f N-octadecyl-N'-cyclo-hexylurea | 190 | yellow |
| 10 g N-octadecyl-acetamide | 230 | yellow |

EXAMPLE 11

About 250 parts of 4,4'-diisocyanato diphenyl methane are mixed at about 60° C. with about 25 parts of powdered nylon 66. The mixture is heated for about 2 hours at about 220° C. After this period of time the NCO content of the mixture has dropped from about 30 to about 21.1%. The reaction mixture is a highly viscous paste. The IR spectrum reveals the typical edge for carbodiimides at 4.8μ. After storage during several days at room temperature the IR spectrum reveals an additional edge at 5.8μ which edge is typical for carbodiimide-isocyanate-adducts.

It is, of course, to be understood that any of the catalysts mentioned above or any of the isocyanates may be used in place of those of the examples.

Although the invention has been described in considerable detail in the foregoing, it is to be understood that such detail is solely for the purpose of illustration and that many variations can be made by those skilled in the art without departing from the spirit and scope of the invention.

What is claimed is:

1. A method for preparing carbodiimides which comprises heating an organic isocyanate at a temperature of at least about 150° C. in the presence of a catalytic amount of a catalyst having the formula:

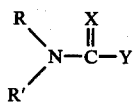

wherein

R and R' are the same or different and represent hydrogen, alkyl, aryl and when joined together form a heterocyclic ring;

Y is hydrogen, alkyl, chloroalkyl, aryl, alkoxyphosphono and

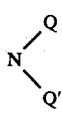

wherein Q is hydrogen, alkyl, or aryl; Q' is hydrogen, alkyl, aryl, COR" and SO$_2$R", wherein R" is alkyl or aryl, and when Y is joined together with R, they form a heterocyclic ring; and X is oxygen or sulfur.

2. The process of claim 1 wherein X is oxygen.

3. The process of claim 1 wherein the isocyanate is 4,4'-diphenyl methane diisocyanate.

4. The process of claim 1 wherein the catalyst is used in an amount of from about 0.2 mol percent to about 5 mol percent based on the quantity of isocyanate.

5. The process of claim 1 wherein the reaction is terminated by cooling after about 33 percent of the —NCO groups have reacted.

6. The process of claim 1 wherein the catalyst is produced in situ by reaction with isocyanate by the addition of a member selected from the group consisting of water, hydrogen sulphide, ammonia, aniline, 2,6-diisopropyl aniline, morpholine, piperazine, ethanol amine, diethanol-amine, acetic acid, butyric acid, thiobutyric acid, lactic acid, oxalic acid, salicylic acid, benzene-sulfonic acid amide, p-toluene sulphonic acid methyl amide and benzene sulphonic acid.

7. A method for preparing carbodiimides which comprises heating an organic isocyanate at a temperature of at least about 150° C in the presence of a catalytic amount of a catalyst selected from the group consisting of urea, monomethylurea, N,N-dimethyl urea, N,N'-diethylurea, N,N'-diethyl-N-methylthiourea, diphenylurea, diphenylthiourea, N-methyl-N'-dimethylurea, N-phenyl-N'-ethylurea, phenylthiourea, N,N-diphenyl-N'-dimethylurea, tetramethylurea, 1,3,5-triphenylbiuret, 1,3-diphenyl-5,5'-dimethylbiuret, 1,3-diphenyl-allophanic acid methyl ester, formanilide, acetamide, methylacetamide, dimethyl acetamide, propionic acid morpholide, bis-(benzoyl)-piperazine, benzoyl piperazine, benzoyl piperidine, benzanilide, acetanilide, N-ethyl-benzanilide, chloroacetamide, thioacetamide, thiobutyric acid anilide, maleic acid hydrazide, caprolactam, N-methylcaprolactam, dodecane lactam, phthalimide, isatin, 1,2,3,6-tetrahydrophthalimide, naphtholactam-1,8,pyrrolidone-(2), piperazine-2,5-dione, saccharin, barbituric acid, diethyl-barbituric acid, rhodamine, vinyl acetamide, p-toluene-sulphonylurea, N-phenylsulphonyl-N'-methylurea, N-phenylsulphonyl-N'-phenylurea, phenylsulphonyl-N,N'-diphenylurea, 4-acetylaminobenzene-sulphonylurea, acetylpropionylurea or benzoylurea, N-acetyl-N-methylurea, benzoylthiourea, N-propionyl-N'-phenylurea, dimethoxyphosphonoform methylanilide, diethoxy-phosphonoform anilide, diethoxyphosphonoform naphthylamide and bis-(2-chloroethoxy)-phosphonoform-N-methylanilide.

8. A method for preparing carbodiimides which comprises heating an organic isocyanate at a temperature of at least about 150° C. in the presence of a catalytic amount of a catalyst selected from the group consisting of acetamide, N,N'-diphenylthiourea, urea, acetanilide, N-methylacetanilide, caprolactam, tetramethylurea, phenyldimethylurea, dimethoxyphosphonoform-N-methylanilide, diethoxyphosphonoform diphenylamide, diethoxyphosphonoform-N-methyl-N-α-naphthlformamide, diethoxyphosphono-ethylformamide, diethoxyphosphono-dimethylformamide.

* * * * *